United States Patent
Hunter et al.

(10) Patent No.: US 8,074,662 B2
(45) Date of Patent: *Dec. 13, 2011

(54) SURGICAL COMMUNICATION AND POWER SYSTEM

(75) Inventors: Mark W Hunter, Broomfield, CO (US); Paul Kessman, Broomfield, CO (US); Brad Jascob, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1284 days.

This patent is subject to a terminal disclaimer.

(21) Appl. No.: 11/497,028

(22) Filed: Jul. 31, 2006

(65) Prior Publication Data

US 2006/0278247 A1 Dec. 14, 2006

Related U.S. Application Data

(63) Continuation of application No. 10/245,843, filed on Sep. 16, 2002, now Pat. No. 7,152,608, which is a continuation of application No. 09/428,722, filed on Oct. 28, 1999, now Pat. No. 6,474,341.

(51) Int. Cl.
*A61B 19/00* (2006.01)

(52) U.S. Cl. ....................................................... 128/899

(58) Field of Classification Search .................. 128/899; 600/587, 591, 300, 301, 549, 509, 424, 426, 600/407, 437, 526; 33/700; 73/1.79; 606/1; 607/32; 340/10.6, 10.33, 10.41; 324/652, 324/207.11, 207.15, 207.17, 207.26; 427/429; 343/718; 713/320; 700/225; 705/22; 709/220; 222/81, 88, 325; 141/330, 367, 375; 342/451

See application file for complete search history.

(56) References Cited

U.S. PATENT DOCUMENTS

| | | | |
|---|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |

(Continued)

FOREIGN PATENT DOCUMENTS

CA 964149 A1 3/1975

(Continued)

OTHER PUBLICATIONS

Adams et al., Computer-Assisted Surgery, IEEE Computer Graphics & Applications, pp. 43-51, (May 1990).

(Continued)

*Primary Examiner* — Brian Szmal
(74) *Attorney, Agent, or Firm* — Harness, Dickey

(57) ABSTRACT

A system operable to assist in a surgical procedure. The system can include a surgical navigation system that can be used to assist in determining a position of the surgical instrument, an information of an anatomical body, information regarding an anatomical structure, or combinations thereof. The system can further display the positional information or the anatomical or physiological information on a display.

34 Claims, 6 Drawing Sheets

U.S. PATENT DOCUMENTS

| | | | |
|---|---|---|---|
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,399,441 A | 8/1983 | Vaughan et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Bludermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,819,655 A * | 4/1989 | Webler .......................... 600/526 |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A * | 7/1990 | Blood ....................... 324/207.17 |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |

| Patent No. | Date | Inventor(s) |
|---|---|---|
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vikomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,243,984 A | 9/1993 | Ogura et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,262,772 A | 11/1993 | Urbas et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,332,971 A | 7/1994 | Aubert |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Müller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,123 A | 10/1995 | Unger |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,109 A | 11/1996 | Bertagnoli |

| Patent No. | Date | Inventor(s) | Patent No. | Date | Inventor(s) |
|---|---|---|---|---|---|
| 5,572,999 A | 11/1996 | Funda et al. | 5,787,886 A | 8/1998 | Kelly et al. |
| 5,573,533 A | 11/1996 | Strul | 5,792,055 A | 8/1998 | McKinnon |
| 5,575,794 A | 11/1996 | Walus et al. | 5,795,294 A | 8/1998 | Luber et al. |
| 5,575,798 A | 11/1996 | Koutrouvelis | 5,797,849 A | 8/1998 | Vesely et al. |
| 5,583,909 A | 12/1996 | Hanover | 5,799,055 A | 8/1998 | Peshkin et al. |
| 5,588,430 A | 12/1996 | Bova et al. | 5,799,099 A | 8/1998 | Wang et al. |
| 5,590,215 A | 12/1996 | Allen | 5,800,352 A | 9/1998 | Ferre et al. |
| 5,592,939 A | 1/1997 | Martinelli | 5,800,535 A | 9/1998 | Howard, III |
| 5,595,193 A | 1/1997 | Walus et al. | 5,802,719 A | 9/1998 | O'Farrell, Jr. et al. |
| 5,596,228 A | 1/1997 | Anderton et al. | 5,803,089 A | 9/1998 | Ferre et al. |
| 5,600,330 A | 2/1997 | Blood | 5,807,252 A | 9/1998 | Hassfeld et al. |
| 5,603,318 A | 2/1997 | Heilbrun et al. | 5,810,008 A | 9/1998 | Dekel et al. |
| 5,611,025 A | 3/1997 | Lorensen et al. | 5,810,728 A | 9/1998 | Kuhn |
| 5,617,462 A | 4/1997 | Spratt | 5,810,735 A | 9/1998 | Halperin et al. |
| 5,617,857 A | 4/1997 | Chader et al. | 5,820,553 A | 10/1998 | Hughes |
| 5,619,261 A | 4/1997 | Anderton | 5,823,192 A | 10/1998 | Kalend et al. |
| 5,622,169 A | 4/1997 | Golden et al. | 5,823,958 A | 10/1998 | Truppe |
| 5,622,170 A | 4/1997 | Schulz | 5,828,725 A | 10/1998 | Levinson |
| 5,627,873 A | 5/1997 | Hanover et al. | 5,828,770 A | 10/1998 | Leis et al. |
| 5,628,315 A | 5/1997 | Vilsmeier et al. | 5,829,444 A | 11/1998 | Ferre et al. |
| 5,630,431 A | 5/1997 | Taylor | 5,831,260 A | 11/1998 | Hansen |
| 5,636,644 A | 6/1997 | Hart et al. | 5,833,608 A | 11/1998 | Acker |
| 5,638,819 A | 6/1997 | Manwaring et al. | 5,834,759 A | 11/1998 | Glossop |
| 5,640,170 A | 6/1997 | Anderson | 5,836,954 A | 11/1998 | Heilbrun et al. |
| 5,642,395 A | 6/1997 | Anderton et al. | 5,840,024 A | 11/1998 | Taniguchi et al. |
| 5,643,268 A | 7/1997 | Vilsmeier et al. | 5,840,025 A | 11/1998 | Ben-Haim |
| 5,645,065 A | 7/1997 | Shapiro et al. | 5,843,076 A | 12/1998 | Webster, Jr. et al. |
| 5,646,524 A | 7/1997 | Gilboa | 5,848,967 A | 12/1998 | Cosman |
| 5,647,361 A | 7/1997 | Damadian | 5,851,183 A | 12/1998 | Bucholz |
| 5,662,111 A | 9/1997 | Cosman | 5,865,846 A | 2/1999 | Bryan et al. |
| 5,664,001 A | 9/1997 | Tachibana et al. | 5,868,674 A | 2/1999 | Glowinski et al. |
| 5,674,296 A | 10/1997 | Bryan et al. | 5,868,675 A | 2/1999 | Henrion et al. |
| 5,676,673 A | 10/1997 | Ferre et al. | 5,871,445 A | 2/1999 | Bucholz |
| 5,681,260 A | 10/1997 | Ueda et al. | 5,871,455 A | 2/1999 | Ueno |
| 5,682,886 A | 11/1997 | Delp et al. | 5,871,487 A | 2/1999 | Warner et al. |
| 5,682,890 A | 11/1997 | Kormos et al. | 5,873,822 A | 2/1999 | Ferre et al. |
| 5,690,108 A | 11/1997 | Chakeres | 5,882,304 A | 3/1999 | Ehnholm et al. |
| 5,694,945 A | 12/1997 | Ben-Haim | 5,884,410 A | 3/1999 | Prinz |
| 5,695,500 A | 12/1997 | Taylor et al. | 5,887,176 A * | 3/1999 | Griffith et al. ................ 713/320 |
| 5,695,501 A | 12/1997 | Carol et al. | 5,889,834 A | 3/1999 | Vilsmeier et al. |
| 5,696,500 A | 12/1997 | Taylor et al. | 5,891,034 A | 4/1999 | Bucholz |
| 5,697,377 A | 12/1997 | Wittkampf | 5,891,157 A | 4/1999 | Day et al. |
| 5,702,406 A | 12/1997 | Vilsmeier et al. | 5,904,691 A | 5/1999 | Barnett et al. |
| 5,711,299 A | 1/1998 | Manwaring et al. | 5,907,395 A | 5/1999 | Schulz et al. |
| 5,713,946 A | 2/1998 | Ben-Haim | 5,913,820 A | 6/1999 | Bladen et al. |
| 5,715,822 A | 2/1998 | Watkins | 5,920,395 A | 7/1999 | Schulz |
| 5,715,836 A | 2/1998 | Kliegis et al. | 5,921,992 A | 7/1999 | Costales et al. |
| 5,718,241 A | 2/1998 | Ben-Haim et al. | 5,923,727 A | 7/1999 | Navab |
| 5,727,552 A | 3/1998 | Ryan | 5,928,248 A | 7/1999 | Acker |
| 5,727,553 A | 3/1998 | Saad | 5,938,603 A | 8/1999 | Ponzi |
| 5,729,129 A | 3/1998 | Acker | 5,938,694 A | 8/1999 | Jaraczewski et al. |
| 5,730,129 A | 3/1998 | Darrow et al. | 5,947,980 A | 9/1999 | Jensen et al. |
| 5,730,130 A | 3/1998 | Fitzpatrick et al. | 5,947,981 A | 9/1999 | Cosman |
| 5,732,703 A | 3/1998 | Kalfas et al. | 5,950,629 A | 9/1999 | Taylor et al. |
| 5,735,278 A | 4/1998 | Hoult et al. | 5,951,475 A | 9/1999 | Gueziec et al. |
| 5,738,096 A | 4/1998 | Ben-Haim | 5,951,571 A | 9/1999 | Audette |
| 5,740,802 A | 4/1998 | Nafis et al. | 5,954,647 A | 9/1999 | Bova et al. |
| 5,741,214 A | 4/1998 | Ouchi et al. | 5,957,844 A | 9/1999 | Dekel et al. |
| 5,742,394 A | 4/1998 | Hansen | 5,964,796 A | 10/1999 | Imran |
| 5,744,953 A | 4/1998 | Hansen | 5,967,980 A | 10/1999 | Ferre et al. |
| 5,748,767 A | 5/1998 | Raab | 5,967,982 A | 10/1999 | Barnett |
| 5,749,362 A | 5/1998 | Funda et al. | 5,968,047 A | 10/1999 | Reed |
| 5,749,835 A | 5/1998 | Glantz | 5,971,997 A | 10/1999 | Guthrie et al. |
| 5,752,513 A | 5/1998 | Acker et al. | 5,976,156 A | 11/1999 | Taylor et al. |
| 5,752,976 A | 5/1998 | Duffin et al. | 5,980,535 A | 11/1999 | Barnett et al. |
| 5,755,725 A | 5/1998 | Druais | 5,983,126 A | 11/1999 | Wittkampf |
| RE35,816 E | 6/1998 | Schulz | 5,987,349 A | 11/1999 | Schulz |
| 5,758,667 A | 6/1998 | Slettenmark | 5,987,960 A | 11/1999 | Messner et al. |
| 5,762,064 A | 6/1998 | Polyani | 5,999,837 A | 12/1999 | Messner et al. |
| 5,767,669 A | 6/1998 | Hansen et al. | 5,999,840 A | 12/1999 | Grimson et al. |
| 5,767,960 A | 6/1998 | Orman | 6,001,130 A | 12/1999 | Bryan et al. |
| 5,769,789 A | 6/1998 | Wang et al. | 6,006,126 A | 12/1999 | Cosman |
| 5,769,843 A | 6/1998 | Abela et al. | 6,006,127 A | 12/1999 | Van Der Brug et al. |
| 5,769,861 A | 6/1998 | Vilsmeier | 6,013,087 A | 1/2000 | Adams et al. |
| 5,772,594 A | 6/1998 | Barrick | 6,014,580 A | 1/2000 | Blume et al. |
| 5,772,661 A | 6/1998 | Michelson | 6,016,439 A | 1/2000 | Acker |
| 5,775,322 A | 7/1998 | Silverstein et al. | 6,019,725 A | 2/2000 | Vesely et al. |
| 5,776,064 A | 7/1998 | Kalfas et al. | 6,024,695 A | 2/2000 | Greenberg et al. |
| 5,782,765 A | 7/1998 | Jonkman | 6,025,725 A | 2/2000 | Gershenfeld et al. |

| | | | | | | |
|---|---|---|---|---|---|---|
| 6,050,724 | A | 4/2000 | Schmitz et al. | DE | 197 47 427 | 10/1997 |
| 6,059,718 | A | 5/2000 | Taniguchi et al. | DE | 197 51 761 | 11/1997 |
| 6,063,022 | A | 5/2000 | Ben-Haim | DE | 198 32 296 | 7/1998 |
| 6,070,761 | A * | 6/2000 | Bloom et al. ............ 222/81 | DE | 10085137 | 7/2002 |
| 6,071,288 | A | 6/2000 | Carol et al. | EP | 0 062 941 | 3/1982 |
| 6,073,043 | A | 6/2000 | Schneider | EP | 0 119 660 | 9/1984 |
| 6,076,008 | A | 6/2000 | Bucholz | EP | 0 155 857 | 1/1985 |
| 6,096,050 | A | 8/2000 | Audette | EP | 0 326 768 | 12/1988 |
| 6,104,944 | A | 8/2000 | Martinelli | EP | 0319844 | 6/1989 |
| 6,118,845 | A | 9/2000 | Simon et al. | EP | 0350996 A1 | 1/1990 |
| 6,122,538 | A | 9/2000 | Sliwa, Jr. et al. | EP | 0 427 358 | 10/1990 |
| 6,122,541 | A | 9/2000 | Cosman et al. | EP | 0419729 A1 | 4/1991 |
| 6,131,396 | A | 10/2000 | Duerr et al. | EP | 0 456 103 | 5/1991 |
| 6,139,183 | A | 10/2000 | Graumann | EP | 0469966 A1 | 2/1992 |
| 6,147,480 | A | 11/2000 | Osadchy et al. | EP | 0655138 B1 | 8/1993 |
| 6,149,592 | A | 11/2000 | Yanof et al. | EP | 0581704 A1 | 2/1994 |
| 6,156,067 | A | 12/2000 | Bryan et al. | EP | 0894473 A2 | 1/1995 |
| 6,161,032 | A | 12/2000 | Acker | EP | 0651968 A1 | 5/1995 |
| 6,165,181 | A | 12/2000 | Heilbrun et al. | EP | 0 908 146 | 10/1998 |
| 6,167,296 | A | 12/2000 | Shahidi | EP | 0 930 046 | 10/1998 |
| 6,172,499 | B1 | 1/2001 | Ashe | FR | 2417970 A1 | 9/1979 |
| 6,175,756 | B1 | 1/2001 | Ferre et al. | FR | 2 618 211 | 7/1987 |
| 6,178,345 | B1 | 1/2001 | Vilsmeier et al. | GB | 2 094 590 | 2/1982 |
| 6,194,639 | B1 | 2/2001 | Botella et al. | GB | 2 164 856 | 10/1984 |
| 6,201,387 | B1 | 3/2001 | Govari | JP | 61-94639 | 10/1984 |
| 6,203,497 | B1 | 3/2001 | Dekel et al. | JP | 62-327 | 6/1985 |
| 6,211,666 | B1 | 4/2001 | Acker | JP | 63-240851 | 3/1987 |
| 6,223,067 | B1 | 4/2001 | Vilsmeier | JP | 3-267054 | 3/1990 |
| 6,233,476 | B1 | 5/2001 | Strommer et al. | JP | 2765738 | 6/1998 |
| 6,246,231 | B1 | 6/2001 | Ashe | WO | WO-8809151 A1 | 12/1988 |
| 6,259,942 | B1 | 7/2001 | Westermann et al. | WO | WO-8905123 | 6/1989 |
| 6,261,247 | B1 * | 7/2001 | Ishikawa et al. ............ 600/587 | WO | WO 90/05494 | 11/1989 |
| 6,273,896 | B1 | 8/2001 | Franck et al. | WO | WO-9103982 A1 | 4/1991 |
| 6,285,902 | B1 | 9/2001 | Kienzle, III et al. | WO | WO-9104711 A1 | 4/1991 |
| 6,298,262 | B1 | 10/2001 | Franck et al. | WO | WO-9107726 A1 | 5/1991 |
| 6,314,310 | B1 | 11/2001 | Ben-Haim et al. | WO | WO-9203090 A1 | 3/1992 |
| 6,332,089 | B1 | 12/2001 | Acker et al. | WO | WO-9206645 A1 | 4/1992 |
| 6,341,231 | B1 | 1/2002 | Ferre et al. | WO | WO 94/04938 | 3/1994 |
| 6,348,058 | B1 | 2/2002 | Melkent et al. | WO | WO 95/07055 | 9/1994 |
| 6,351,659 | B1 | 2/2002 | Vilsmeier | WO | WO-9423647 A1 | 10/1994 |
| 6,381,485 | B1 | 4/2002 | Hunter et al. | WO | WO-9424933 A1 | 11/1994 |
| 6,424,856 | B1 | 7/2002 | Vilsmeier et al. | WO | WO 96/32059 | 11/1995 |
| 6,427,314 | B1 | 8/2002 | Acker | WO | WO 96/11624 | 4/1996 |
| 6,428,547 | B1 | 8/2002 | Vilsmeier et al. | WO | WO 97/49453 | 6/1997 |
| 6,434,415 | B1 | 8/2002 | Foley et al. | WO | WO 97/36192 | 10/1997 |
| 6,437,567 | B1 | 8/2002 | Schenck et al. | WO | WO 99/23956 | 11/1997 |
| 6,445,943 | B1 | 9/2002 | Ferre et al. | WO | WO-9808554 A1 | 3/1998 |
| 6,470,207 | B1 | 10/2002 | Simon et al. | WO | WO 99/15097 | 9/1998 |
| 6,474,341 | B1 | 11/2002 | Hunter et al. | WO | WO-9838908 A1 | 9/1998 |
| 6,478,802 | B2 | 11/2002 | Kienzle, III et al. | WO | WO 99/21498 | 10/1998 |
| 6,484,049 | B1 | 11/2002 | Seeley et al. | WO | WO 99/27839 | 12/1998 |
| 6,490,475 | B1 | 12/2002 | Seeley et al. | WO | WO 99/33406 | 12/1998 |
| 6,493,573 | B1 | 12/2002 | Martinelli et al. | WO | WO 99/38449 | 1/1999 |
| 6,498,944 | B1 | 12/2002 | Ben-Haim et al. | WO | WO 99/52094 | 4/1999 |
| 6,499,488 | B1 | 12/2002 | Hunter et al. | WO | WO 99/26549 | 6/1999 |
| 6,516,046 | B1 | 2/2003 | Fröhlich et al. | WO | WO 99/29253 | 6/1999 |
| 6,527,443 | B1 | 3/2003 | Vilsmeier et al. | WO | WO 99/38208 | 7/1999 |
| 6,551,325 | B2 | 4/2003 | Neubauer et al. | WO | WO-9960939 A1 | 12/1999 |
| 6,584,174 | B2 | 6/2003 | Schubert et al. | WO | WO00/69335 | 11/2000 |
| 6,609,022 | B2 | 8/2003 | Vilsmeier et al. | WO | WO-0130437 A1 | 5/2001 |
| 6,611,700 | B1 | 8/2003 | Vilsmeier et al. | | | |
| 6,640,128 | B2 | 10/2003 | Vilsmeier et al. | | | |
| 6,694,162 | B2 | 2/2004 | Hartlep | | | |
| 6,701,179 | B1 | 3/2004 | Martinelli et al. | | | |
| 7,152,608 | B2 * | 12/2006 | Hunter et al. ............ 128/899 | | | |
| 2001/0007918 | A1 | 7/2001 | Vilsmeier et al. | | | |
| 2002/0095081 | A1 | 7/2002 | Vilsmeier | | | |
| 2004/0024309 | A1 | 2/2004 | Ferre et al. | | | |

FOREIGN PATENT DOCUMENTS

| | | | |
|---|---|---|---|
| DE | 3042343 A1 | 6/1982 | |
| DE | 35 08730 | 3/1985 | |
| DE | 37 17 871 | 5/1987 | |
| DE | 38 38011 | 11/1988 | |
| DE | 3831278 A1 | 3/1989 | |
| DE | 42 13 426 | 4/1992 | |
| DE | 42 25 112 | 7/1992 | |
| DE | 4233978 | 4/1994 | |
| DE | 197 15 202 | 4/1997 | |

OTHER PUBLICATIONS

Bergstrom et al. Sterotaxic Computed Tomography, Am. J. Roentgenol, vol. 127 pp. 167-170 (1976).

Brown, R., M.D., A Stereotactic Head Frame for Use with CT Body Scanners, Investigative Radiology © J.B. Lippincott Company, pp. 300-304 (Jul.-Aug. 1979).

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracing of Bone Fragments During Craniofacial Surgery, Second Annual International Symposium on Medical Robotics and Compter Assisted Surgery, pp. 221-225, (Nov. 1995).

Friets, E.M., et al. A Frameless Sterotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Sterotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging crtical tissues, Sci. Amer., vol. 280, No. 6, pp. 62-69 (Jun. 1999).

Hardy, T., M.D., et al., CASS: A Program for Computer Assisted Sterotaxic Surgery, The Fifth Annual Symposium on Computer Applications in Medical Carel Proceedings, Nov. 1-4, 1981, IEEE, pp. 1116-1126 (1981).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Sterotactic Systems, Clinical Neurosurgery, Chapter 31, pp. 564-581 (1983).

Heilbrun, M.P., et al., Sterotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Kail, B., The Impact of Computer and Imaging Technology on Stereotactic Surgery, Proceedings of the Meeting of the American Society for Sterotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988 pp. 7-17 (Jan. 1988).

Kelly, P.J., Stereotactic Imaging, Surgical Planning and Computer-Assisted Resection of Trancranial Lesions: Methods and Results, Advances and Technical Standards in Neurosurger, vol. 17, pp. 78-118 (1990).

Kim, W.S. et al., A Helmet Mounted Display for Telerobotics, IEEE, pp. 543-547 (1988).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computer Assisted Radiology, pp. 362-366 (Jul. 3-6, 1991).

Kwoh, Y.S., Ph.D., et al., A New Computerized Tomographic-Aided Robotic Stereotaxis System, Robotics Age, vol.7, No. 6, pp. 17-22 (Jun. 1985).

Lavallee, S., et al., Computer Assisted Knee Anterior Cruciate Ligament Reconstruction First Clinical Tests, Proceedings of the First International Symposium of Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformation Using Sonar Stereometry). Ultraschall in Med. 12, pp. 80-83 (1991).

Smith, K.R., et al. Multimodality Image Analysis and Display Methods for Improved Tumor Localization in Stereotactic Neurosurgery, Annul Intl. Conf. of the IEEE Eng. In Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Schreiner, S., et al: "An Ultrasonic Approach to Localization of Fiducial Markers for Interactive, Image-Guided Neurosurgery—Part II: Implementation and Automation" IEEE Transactions on Biomedical Enginerring, US, IEEE, Inc. New York, vol. 45, No. 5, May 1, 1998, pp. 631-641, XP000740789; ISSN: 0018-9294 the whole document.

International Search Report mailed Jan. 6, 2001.

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensional Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May, 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Germano, "Instrumentation, Technique and Technology", Neurosurgery, vol. 37, No. 2, Aug., 1995, pp. 348-350.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Galloway, R.L., Jr. et al, Optical localization for interactive, image-guided neurosurgery, SPIE, vol. 2164, (May 1, 1994) pp. 137-145.

Guthrie, B.L., Graphic-Interactive Cranial Surgery: The Operating Arm System, Handbook of Stereotaxy Using the CRW Apparatus, Chapter 13 (1994) pp. 193-211.

Hamadeh et al, "Kinematic Study of Lumbar Spine Using Functional Radiographies and 3D/2D Registration," TIMC UMR 5525—IMAG (1997).

Klimek, L., et al., Long-Term Experience with Different Types of Localization Systems in Skull-Base Surgery, Ear, Nose & Throat Surgery, Chapter 51 (1996) pp. 635-638.

Lavallee et al., "Computer Assisted Spine Surgery: A Technique For Accurate Transpedicular Screw Fixation Using CT Data and a 3-D Optical Localizer," TIMC, Faculte de Medecine de Grenoble. (1995).

Reinhardt, Hans. F., Neuronavigation: A Ten-Year Review, Neurosurgery (1996) pp. 329-341.

Simon, D.A., Accuracy Validation in Image-Guided Orthopaedic Surgery, Second Annual Intl. Symp. on Med. Rob. an Comp-Assisted surgery, MRCAS (1995) pp. 185-192.

Weese et al., "An Approach to 2D/3D Registration of a Vertebra in 2D X-ray Fluoroscopies with 3D CT Images" (1997) pp. 119-128.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR, pp. 716-722, 1998.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May, 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.

Galloway, R.L., Jr. et al, Optical localization for interactive, image-guided neurosurgery, SPIE, vol. 2164, pp. 137-145 (undated.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun., pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS, pp. 39-46, 1995.

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR, pp. 710-715, 1998.

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Image guided operating robot: a clinical application in stereotactic neurosurgery," Proceedings of the 1992 IEEE International Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," Acta Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS, pp. 185-192, 1995.

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

* cited by examiner

SURGICAL COMMUNICATION AND POWER SYSTEM

CROSS-REFERENCE TO RELATED APPLICATIONS

This application is a continuation of U.S. patent application Ser. No. 10/245,843 filed on Sep. 16, 2002; which is a continuation of U.S. patent application Ser. No. 09/428,722 filed on Oct. 28, 1999, now U.S. Pat. No. 6,474,341, issued on Nov. 5, 2002. The disclosures of the above applications are incorporated herein by reference.

FIELD

The present invention relates to wireless remote medical devices. The invention has particular application when used with a method and system for determining the position of a wireless catheter probe being used during a surgical procedure.

BACKGROUND

Various locating systems have been used in the past to determine the position of an object such as the tip of an endoscope or a catheter within the human body Systems and methods are known for determining the location of a catheter or endoscopic probe inserted into a selected body cavity of a patient undergoing a surgical procedure. For example, there exist systems that may use acoustics, optics, conductance and electromagnetics to locate or "localize" a medical instrument in an anatomical body. In an electromagnetic system, location data may be obtained from electrical measurements of voltage signals that are induced within a sensing coil affixed to the distal end of the catheter prove. A voltage is induced in the sensing coil in response to pre-specified electromagnetic fields that project into the anatomical region of interest which contains all prospective locations of the catheter probe. The electrical measurements of the induced signals may provide sufficient information to compute the angular orientation and the positional coordinates of a coil in a sensor, and hence the catheter probe, which collectively define the location of the coil.

Regardless of the technical particulars of a surgical localization system, each system typically includes a component internal to the patient associated with a medical device and a component external to the patient for calculating the position of the medical instrument.

SUMMARY

The present invention is directed to improving communication links between internal and external surgical navigation components and to providing wireless power to internal components.

The invention in its broadest sense may include one or more of the following aspects alone or in combination with one or more elements:

an apparatus and method for locating a wireless sensor/transmitter within an anatomical body, at least one signal generator for sending reference signals through the anatomical body to be received by the sensor/transmitter and to be wirelessly re-transmitted by the sensor/transmitter as positional signals indicative of a current location of the sensor/transmitter in the anatomical body, a receiver for receiving positional signals from the wireless sensor/transmitter, a processor for computing a position of a wireless sensor/transmitter as a function of the positional signals transmitted to a receiver, and a circuit associated with the processor for outputting position image information to a display device, a wireless sensor/transmitter for use in surgical procedures to track the movement of structures within an anatomical body having a portion for receiving a reference signal from a reference signal generator, and a portion for wirelessly transmitting the reference signal as a positional signal indicative of a current position of the sensor and hence the probe, a sensor having a coil adapted to have a voltage induced therein by a signal generator separated from the coil by a distance, a sensor having a circuit for powering the transmitter using an induced voltage.

It is to be understood that both the foregoing general description and the following detailed description are exemplary and explanatory only and are not restrictive of the invention, as claimed.

The accompanying drawings, which are incorporated into and constitute a part of this specification, illustrate several embodiments of the invention and together with the description, serve to explain the principles of the invention.

DESCRIPTION OF THE VARIOUS EMBODIMENTS

The present invention may be used in connection with any wireless surgical navigation system for determining a position of a medical instrument during surgery including the method and apparatus disclosed in U.S. Pat. No. 5,592,939 to Martinelli, hereby incorporated by reference. For brevity, the details of this system, including the assembly of the coils for generating a magnetic field within an anatomical body sufficient to describe the position of a medical instrument and the algorithm for determining the position of the medical instrument, are not enclosed herein.

Figure 1:
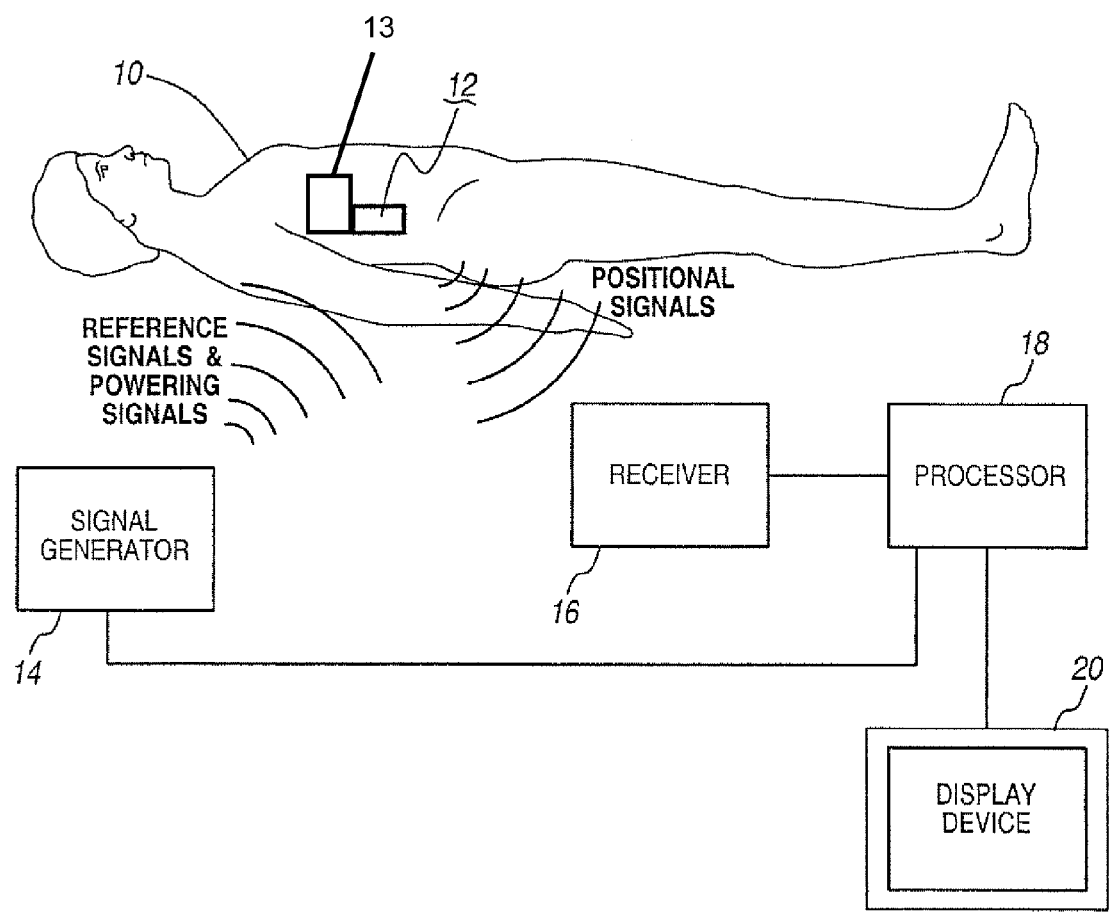
FIG. 1 is a schematic diagram of the system environment in which the features of the present invention may be implemented.

One aspect of the present invention relates to locating a wireless sensor/transmitter associated with a probe, such as a catheter, inside an anatomical body. FIG. 1 illustrates an example of the invention, where the anatomical body 10 is that of a human patient undergoing a surgical or diagnostic procedure. While a human is used in this example, the invention may be used on others such as animals. In accordance with the present invention, there is provided an apparatus for locating the position of a wireless sensor/transmitter within an anatomical body, which apparatus includes at least one signal generator for transmitting reference signals through the anatomical body to be received by the sensor/transmitter and to be wirelessly re-transmitted by the sensor/transmitter as positional signals indicative of a location of the sensor/transmitter in the anatomical body at a given instant of time.

As embodied herein, the signal generator of the invention may include one or more signal generators 14A-14N which include a coil capable of generating an electromagnetic field, described more fully hereinafter. As used herein, a coil refers to an electrically conductive, magnetically sensitive element of the sensor/transmitter that is responsive to time-varying magnetic fields for generating induced voltage signals as a function of, and representative of, the applied time-varying magnetic field. Preferably, signal generator 14 includes multiple coils. Each coil of the signal generator 14 may be activated in succession, each producing a magnetic field within the anatomical body 10 inducing a corresponding voltage signal in a sensing coil 22 of the sensor/transmitter 12.

In the preferred embodiment of the invention, signal generator 14 employs a distinct magnetic assembly so that the voltages induced in a sensing coil 22 corresponding to a transmitted time-dependent magnetic field produce sufficient information to describe the location, i.e. position and orientation, of the sensor/transmitter. The signals produced by the signal generator containing sufficient information to describe the position of the sensor/transmitter are referred to hereinafter as reference signals. Preferably, the reference signals are in the range of 2 KHz to 10 KHz.

Figure 2:
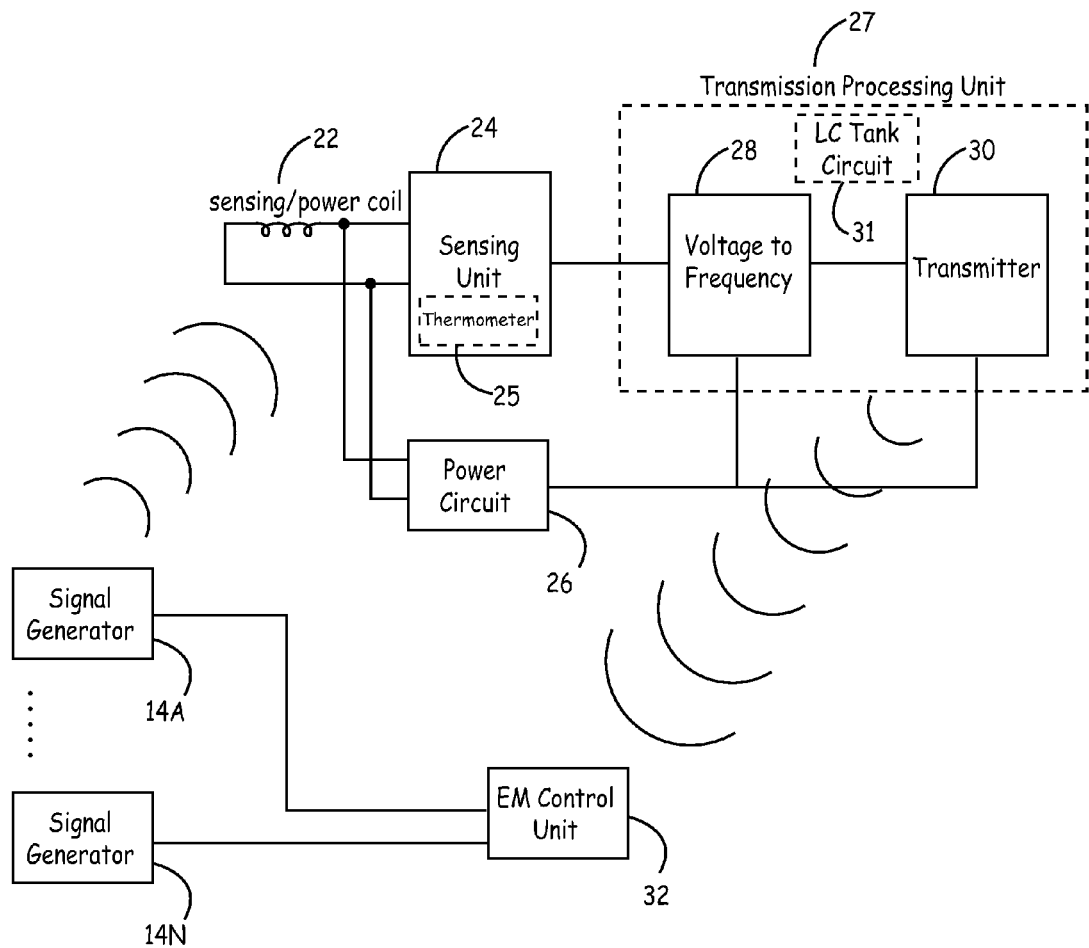
FIG. 2 is a second schematic diagram of the system environment in which the features of the present invention may be implemented.

In the preferred embodiment of the invention, the signal generator 14 is also configured to induce a voltage in the sensing coil of the sensor/transmitter sufficient to power a transmitting portion of the sensor/transmitter. In the preferred embodiment, the signals transmitted by the signal generator for powering the device, hereinafter referred to as powering signals, are frequency multiplexed with the reference signals as illustrated in FIG. 2. In the technique of frequency multiplexing, the frequency ranges of the reference signal and powering signal are modulated so as to occupy mutually exclusive frequency intervals. This technique allows the signals to be transmitted simultaneously over a common channel, such as a wireless channel, while keeping the signals apart so that they do not interfere with each other. The reference and positional signals are preferably frequency modulated (FM) for a better utilization of both power and bandwidth and an increased threshold to noise. However, amplitude modulation (AM) may also be used within the scope of the invention.

Alternatively, the powering signals may be transmitted by separate signal generators, each at a differing frequencies. Preferably, the powering signals are transmitted at higher frequencies than the reference signals. The preferred range of frequencies for the powering signals is 20 KHz to 200 KHz. Utilizing a higher modulation frequency than the reference signals enables the powering signals to couple better with the wireless sensor/transmitter, thereby enabling a greater transfer of power to the device. Using the preferred, mutually exclusive, frequency ranges for the transmission of the reference and powering signals, enables a single coil in the wireless sensor/transmitter to simultaneously receive both signals without interference of the signals.

Also in accordance with the present invention, there is provided an apparatus for locating a wireless sensor/transmitter within an anatomical body including a receiver for receiving positional signals from the wireless sensor/transmitter. As embodied herein, the receiver may include a receiver 16 that is adapted to receive radio-frequency (RF) mode positional signals or magnetic field mode positional signals.

In the preferred embodiment, the receiver 16 is adapted to receive RF signals. The RF signals may be amplitude modulated or frequency modulated signals in the frequency range of 1 MHz to 1 GHz. In the RF embodiment, there is no need to time multiplex the reference signals transmitted by the signal generator with the positional signals re-transmitted by the wireless sensor/transmitter since the signal types, magnetic and radio-frequency, are different. In other words, there is no concern with interference between the reference signal and the positional signal in the RF embodiment since the receiver 16 does not have difficulty in separating the reference signal from the positional signal.

However, a concern with interference between the reference signal and the positional signal may exist if the reference signal and the positional signal are both transmitted as a magnetic field without mutually exclusive frequency intervals. Therefore, in another embodiment in which the receiver is adapted to receive magnetic field mode positional signals, the transmission of the reference signals from the signal generator 14 and the re-transmission of the positional signals from the wireless sensor/transmitter 12 may be time multiplexed. That is, each signal may engage a wireless communication channel for only a fraction of an interval on a periodic basis, so that they may jointly utilize the common channel on a time-shared basis. In so doing, the signals are kept apart so that they do not interfere with each other.

However, in the preferred embodiment of the receiver adapted to receive magnetic field mode positional signals, the frequency range of the positional signal is differed from the reference signal by a voltage-to-frequency converter within the sensor/transmitter so that time multiplexing is unnecessary, thereby avoiding loss of cycles of each signal and an accompanying reduced data rate. In this case, the device may receive continuous powering signals and reference signals from the signal generator.

Also in accordance with the present invention, there is provided an apparatus for locating a wireless sensor/transmitter within an anatomical body including a processor for computing a position of the wireless sensor/transmitter as a function of the positional signals transmitted to the receiver. The processor may determine the position of the sensor/transmitter by solving equations representing signals induced in the sensing coil in response to a sequence of magnetic fields generated successively within the anatomical body. In the preferred embodiment of the present invention, the processor begins determining the position of the sensor/transmitter by first determining the angular orientation of the sensing coil and then using the orientation of the coil to further determine the position of the coil. However, as previously mentioned, the present invention is not limited to any specific method of determining the position of the wireless sensor/transmitter.

Another function of the processor may be to electrically activate the coil(s) of signal generator 14 to generate the desired electromagnetic fields. Yet another function of the processor may be to regulate the timing of the apparatus so that the processor may later recall which induced voltage corresponds to a given coil set within signal generator 14 when determining a position of the sensor/transmitter.

Also in accordance with the present invention, there is provided an apparatus for locating a wireless sensor/transmitter within an anatomical body including a circuit associated with the processor for outputting position image information to a display device. As embodied herein, the display device may include a display device 20, such as, for example, a CRT, LCD or other display suitable for displaying position image information for surgical procedures. The examples given are illustrative only. Display device 20 is not limited to any particular display.

FIG. 2 provides another example of a system environment wherein receiver 16, processor 18, and display device 20 are combined into an electromagnetic control unit 32. FIG. 2 illustrates how the electromagnetic control unit, or localizer, includes critical elements in determining the position of a wireless sensor/transmitter.

Figure 4:
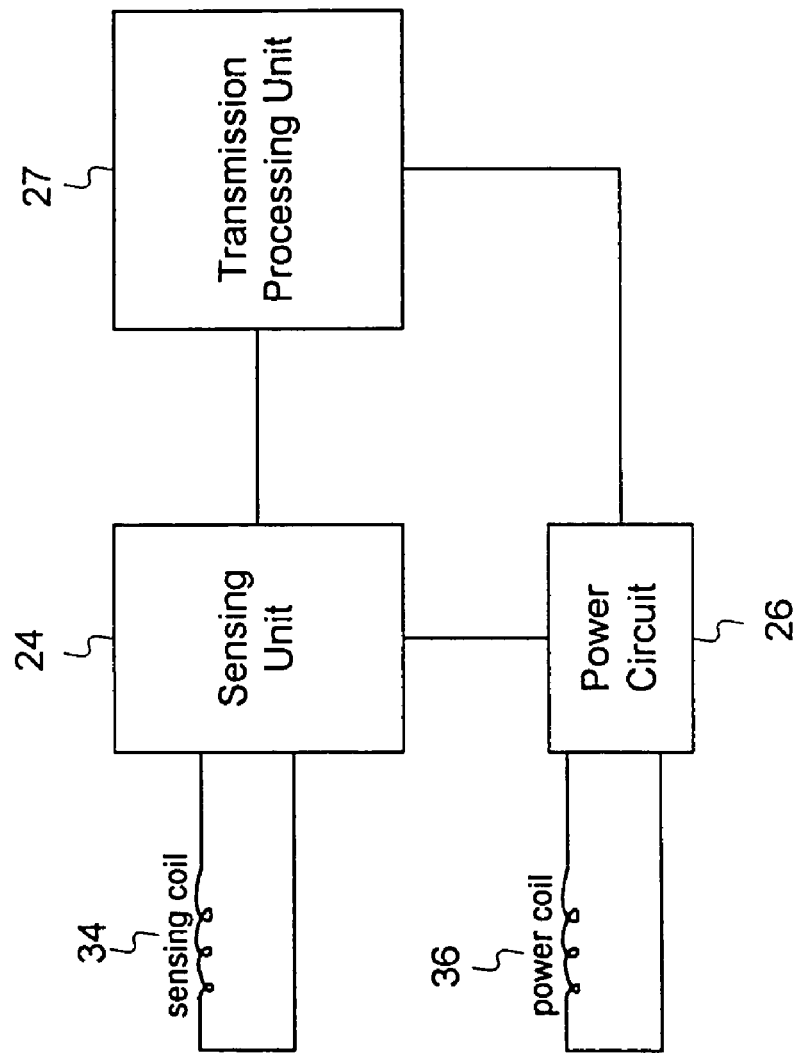

Also in accordance with the present invention, there is provided a wireless sensor/transmitter for use in surgical procedures to track the movement of structures within an anatomical body, such as organs and tissues, including a portion for receiving a reference signal from a reference signal generator. The portion for receiving a reference signal includes a coil adapted to have a voltage induced by the signal generator. For example, FIG. 4 illustrates a sensing coil 34 on which the reference signal may induce voltage corresponding to a positional signal indicative of a current position.

In a preferred embodiment of the invention, a sensing coil is not limited to receiving reference signals to induce voltage corresponding to positional signals. Instead, the sensing coil may also receive powering signals which induce sufficient voltage to power the transmitter. In the preferred embodiment of the device illustrated in FIGS. 2 and 3, sensing coil/power coil 22 induces voltage corresponding to both reference and positional signals from signal generator 14.

Figure 3:
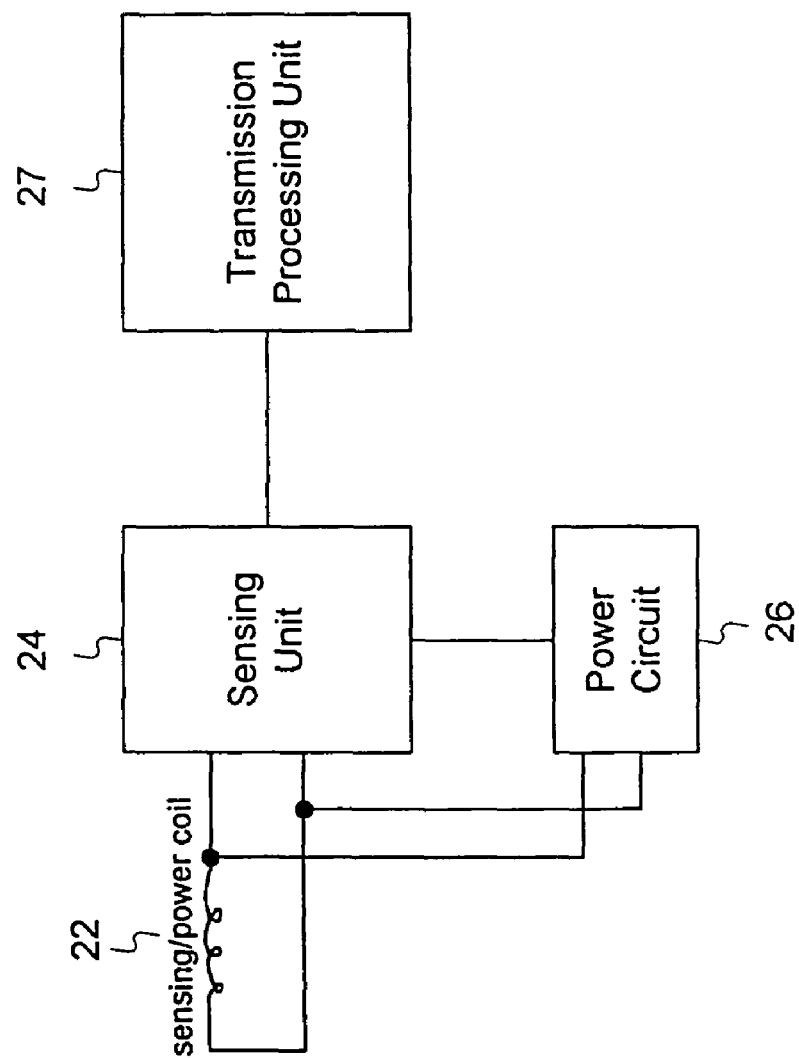
FIGS. 3-5 are schematic views of various embodiments of wireless sensor/transmitters in accordance with the invention.

As embodied herein, the portion for receiving a reference signal further includes a sensing unit and a powering circuit, such as sensing unit 24 and power circuit 26 shown in FIGS. 2 and 3. Sensing unit 24 and power circuit 26 of the preferred embodiment each may receive an induced voltage signal due to a frequency multiplexed reference signal and powering signal on sensing/powering coil 22. Sensing unit 24 and powering circuit 26 both may separate the voltage signals induced by the multiplexed magnetic signals into positional and powering signals. Standard frequency demodulating techniques are used for separating the signals.

Upon separation of the positional and powering signals, sensing unit 24 may measure the induced voltage signal portion corresponding to a reference signal as a positional signal indicative of a current position of a wireless sensor/transmitter 12. The positional signal is retained for further processing and re-transmission by a transmitting portion of the sensor/transmitter. Similarly, power circuit 26 may retain the induced voltage signal portion corresponding to a powering signal for use by the power circuit in producing power. Powering circuit 26 may rectify the induced voltage generated on a coil by the powering signals to produce DC power. Powering circuit 28 may store the DC power using a capacitor, small battery, or other storage means for later use by one or more components of the wireless sensor/transmitter. In a preferred embodiment, the DC power is produced continuously by powering circuit 26 and storage is not necessary.

In another embodiment shown in FIG. 4, separate coils are used for receiving, respectively, the reference signals and the powering signals. The processing performed by sensing unit 26 and power circuit 26 on the induced voltage signals corresponding to a frequency multiplexed reference signal and powering signal remain unchanged. Due to space constraints of the wireless sensor/transmitter, the aforementioned embodiment which utilizes a single coil in the system for powering the transmitter is preferred.

Also in accordance with the present invention, there is provided a wireless sensor/transmitter for use in surgical procedures to track the movement of structures within an anatomical body including a portion for wirelessly transmitting the reference signal as a positional signal indicative of a current position of the sensor. As illustrated in FIG. 2, the transmitting portion may include a transmission processing unit 27 that processes positional signals for transmission and then transmits the positional signals to a receiver.

Transmission processing unit 27 may include a voltage-to-frequency converter, embodied herein as voltage-to-frequency converter 28. Voltage-to-frequency converter converts the induced voltage signal corresponding to the position of a wireless sensor/transmitter to a corresponding signal with a transmission frequency which is proportional to the measured voltage. The frequencies produced by the converter may be made to vary within a given range. Preferably, voltage-to-frequency converter 28 is powered by the rectifier circuit of power circuit 26. In other embodiments, however, a battery or other power source may power voltage-to-frequency converter 28.

Transmission processing unit 27 also may include a transmitter, embodied herein as transmitter 30. Transmitter 30, and hence transmission processing unit 27, may be configured for RF transmission or magnetic field transmission.

If RF transmission is employed, transmitter 30 may include an antenna to retransmit the positional signal to a receiver. The positional signal is preferably transmitted by the sensor/transmitter in the frequency range of 1 MHz to 1 GHz, where voltage-to-frequency converter 28 is adapted to produce the positional signal in the given frequency range according to the measured induced voltage. In the RF embodiment, as previously mentioned, transmitter 30 does not need to time-multiplex the re-transmission of positional signals with the transmission of reference signals since no interference between the signals occurs.

Figure 5:
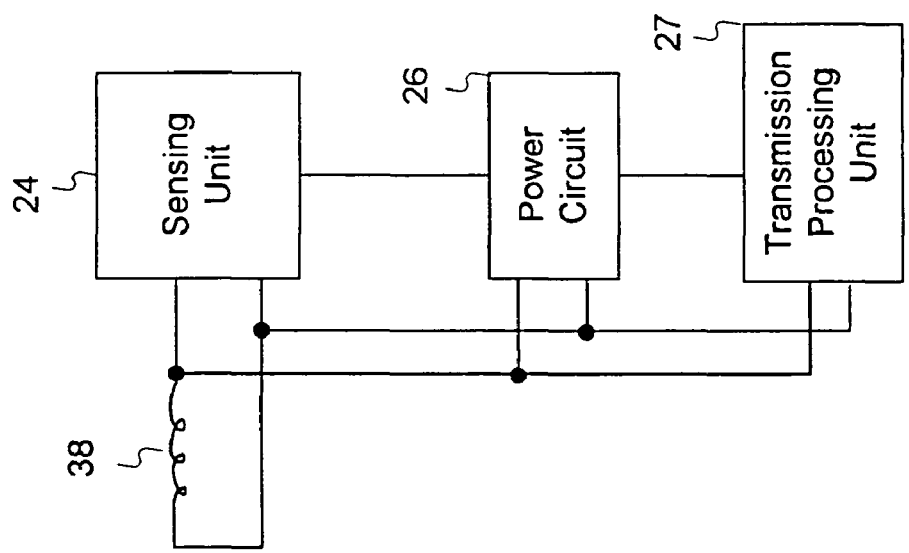

If magnetic field transmission is employed, transmitter 30 may include a coil arrangement to transmit the positional signal to the receiver. Transmitter 30 may have its own magnetic coil or it may share the coil of the sensing unit. As shown in FIG. 5, the transmitter may share a coil 38 that is used by both sensing unit 24 and power circuit 26. The positional signal is preferably transmitted by the sensor/transmitter in the frequency range of 50 KHz to 200 KHz. Using voltage-to-frequency converter 28 to produce the positional signal in the preferred frequency range according to the measured induced voltage, the system may multiplex the transmitted reference signal and re-transmitted positional signal in frequency, rather than in time. While another embodiment may be to time multiplex the reference and positional signals during magnetic field transmission, frequency multiplexing is preferred as it allows both signals to be transmitted simultaneously.

Alternatively, the transmitting portion of the wireless sensor/transmitter may include an inductor-capacitor (LC) tank circuit 31 instead of a coil to transmit the positional signal via a magnetic field mode to the receiver. If an LC tank circuit 31 is used instead of a coil for magnetic transmission of the positional signal, the LC tank circuit 31 is tuned to a resonant frequency to receive the magnetic field and transmit it to the wireless magnetic receiver. As stated above, the position signal may have its frequencies changed from those of the reference signal to avoid time multiplexing during transmission, or it may use time multiplexing for simplification of the processing and transmission of the positional signal upon receiving the same.

The transmitting portion may also transmit the positional signal via digital RF transmission. If digital RF transmission is chosen, the transmission processing unit 27 may include an analog-to-digital (A/ND) converter for converting the analog signal to digital. The A/D converter may include an A/D converter 40 shown in FIG. 6. The A/D converter 40 may be interfaced to a signal transmission module for direct transmission after conversion, or it may be interfaced to a digital signal processor (DSP) system for further processing.

Figure 6:
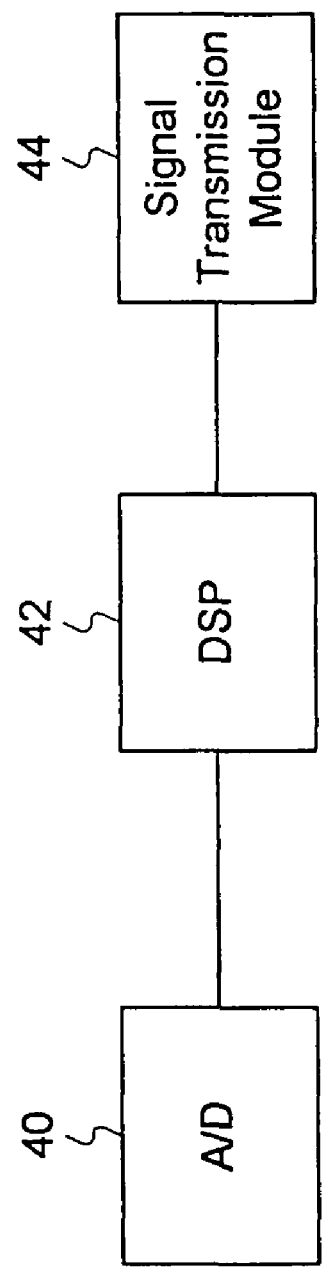
FIG. 6 is a schematic view of one embodiment of a transmitter in a wireless sensor/transmitter.

In a preferred embodiment illustrated in FIG. 6, the transmission processing unit further includes a DSP system 42. A DSP system allows for more effective use of the transmission bandwidth by processing the positional signal using conventional coding and compression techniques. The DSP system may be interfaced to a signal transmission module 44. Signal transmission module 44 of the present invention uses techniques similar to wireless modems or digital RF techniques to transmit the signal to the wireless receiver. In another embodiment, the DSP may be integrated with the A/D converter to conserve space. The A/D converter, DSP, and signal transmission module are preferably powered by power circuit 26. However, one or more of the above devices may be powered by a battery or other power source.

Other embodiments of the invention will be apparent to those skilled in the art from consideration of the specification and practice of the invention disclosed herein. For example, instead of using the induced voltage on the sensing coil to find the position of a wireless sensor/transmitter, one could induce voltage on a sensing coil of a probe to power any sensor or battery in the anatomical body. One sensor receiving power, for example, may be a thermometer 25 for measuring temperature within the chamber of the heart 13.

Another embodiment of the invention may derive power in a wireless sensor/transmitter through an optical means. For example, the power coil of the present invention could be substituted with a photocell or solar cell to obtain optical power from an optical transmitter, such as infrared or a light-emitting diode (LED), and convert it to electrical power for use by the device. Moreover, any transmitter in the system may be substituted with an optical transmission means. Optical transmission means may be combined with other transmission means, such as magnetic or RF transmissions. For example, the sensing coil may receive electromagnetic signals for powering transmitter 30, while transmitter 30 may generate optical signals to receiver 16. The present invention allows various types of transmission.

What is claimed is:

1. A surgical navigation system for use during a surgical procedure on an anatomical body, the surgical navigation system comprising:
    a signal generator configured to wirelessly transmit signals from a site remote from the anatomical body, the signals including reference signals and powering signals that are frequency multiplexed;
    a first wireless sensor/transmitter adapted to be positioned relative to the anatomical body, the wireless sensor/transmitter configured to: (i) receive the signals from the signal generator, (ii) wirelessly transmit information signals, (iii) utilize the powering signals to power the first wireless sensor/transmitter, and (iv) utilize the reference signals to generate the information signals; and
    a processor configured to determine an angular orientation and a position of the first wireless sensor/transmitter based on the information signals.

2. The surgical navigation system of claim 1, further comprising:
    a display to display position information.

3. The surgical navigation system of claim 2, wherein said information signals are sensed signals from the anatomical body.

4. The surgical navigation system of claim 3, wherein the information signals are a temperature measured of the anatomical body.

5. The surgical navigation system of claim 3, wherein the information signals are displayed on the display with position information of the first wireless sensor/transmitter.

6. The surgical navigation system of claim 2, wherein said signal generator includes an electromagnetic field generator coil.

7. The surgical navigation system of claim 6, wherein the first wireless sensor/transmitter includes a sensing coil and a power coil.

8. The surgical navigation system of claim 7, wherein the signal generator includes a plurality of coils configured to produce an electromagnetic field each in succession to induce a signal in the first wireless sensor/transmitter.

9. The surgical navigation system of claim 7, wherein the sensing coil and the power coil are configured to separate the signals to both power the wireless sensor/transmitter and determine position information of the wireless sensor/transmitter.

10. The surgical navigation system of claim 9, wherein the power coil is configured to rectify an induced voltage from the multiplex signal to create DC power.

11. The surgical navigation system of claim 10, wherein the first wireless sensor/transmitter further includes at least one of a capacitor, a battery, a power storage system or combinations thereof.

12. The surgical navigation system of claim 7, wherein the sensing coil and the power coil are a single coil.

13. The surgical navigation system of claim 1, wherein said first wireless sensor/transmitter is formed as a component internal to the anatomical body.

14. The surgical navigation system of claim 1, further comprising a second wireless sensor/transmitter.

15. The surgical navigation system of claim 1, wherein the first wireless sensor/transmitter includes an inductor-capacitor tank circuit configured to transmit via a magnetic field mode the information signal.

16. The surgical navigation system of claim 15, wherein the information signal is a positional signal.

17. The surgical navigation system of claim 1, further comprising a receiver coupled to the processor, the receiver configured to wirelessly receive the information signals from the first wireless sensor/transmitter.

18. A surgical navigation apparatus for use during a surgical procedure on an anatomical body, the surgical navigation apparatus comprising:
    a signal generator configured to wirelessly transmit signals from a site remote from the anatomical body, the signal generator including an electromagnetic field generator coil and the signals including reference signals and powering signals that are frequency multiplexed;
    a first wireless sensor/transmitter including a sensing coil and a power coil, the first wireless sensor/transmitter:
        adapted to be positioned relative to the anatomical body,
        configured to receive the signals from the signal generator,
        configured to wirelessly transmit information signals indicative of information regarding the surgical procedure, wherein the information signals include sensed signals from the anatomical body,
        configured to utilize the powering signals to power the first wireless sensor/transmitter, and
        configured to utilize the reference signals to generate the information signals;
    a processor configured to determine an angular orientation and a position of the first wireless sensor/transmitter based at least in part on the information signals; and
    a display operably connected to the processor and configured to display the angular orientation and position of the first wireless sensor/transmitter.

19. The surgical navigational apparatus of claim 18, wherein the signal generator includes a plurality of signal generators.

20. The surgical navigational apparatus of claim 19, wherein the plurality of signal generators include a plurality of coils configured to be energized in succession.

21. The surgical navigational apparatus of claim 20, wherein the first wireless sensor/transmitter is configured to receive a magnetic field signal in succession from each of the plurality of signal generators.

22. The surgical navigation apparatus of claim 21, wherein the first wireless sensor/transmitter includes a coil in which a voltage is induced by the magnetic field signal.

23. The surgical navigation apparatus of claim 18, wherein the first wireless sensor/transmitter includes an inductor-capacitor tank circuit.

24. The surgical navigation apparatus of claim 18, wherein the first wireless sensor/transmitter includes a thermometer.

25. The surgical navigation apparatus of claim 18, wherein the anatomical body includes a heart.

26. The surgical navigation apparatus of claim 18, wherein the first wireless sensor/transmitter includes a plurality of coils to receive the signal transmitted from the signal generator.

27. The surgical navigation apparatus of claim 18, wherein the information signal is a temperature measured of the anatomical body.

28. The surgical navigation apparatus of claim 27, wherein the temperature is a temperature within a chamber of a heart of the anatomical body.

29. The surgical navigation apparatus of claim 18, wherein the sensed signals from the anatomical body include physiological information of the anatomical body.

30. The surgical navigation apparatus of claim 18, wherein said first wireless sensor/transmitter is formed as a component internal to the anatomical body.

31. The surgical navigation apparatus of claim 18, wherein the signal generator includes a coil operable to generate an electromagnetic field.

32. The surgical navigation apparatus of claim 31, wherein the signal generator includes a plurality of coils configured to produce an electromagnetic field each in succession to induce a signal in the first wireless sensor/transmitter.

33. The surgical navigation apparatus of claim 18, wherein the first wireless sensor/transmitter includes a single coil configured to receive the signal transmitted from the signal generator.

34. The surgical navigation apparatus of claim 18, further comprising a receiver coupled to the processor, the receiver configured to wirelessly receive the information signals from the first wireless sensor/transmitter.

\* \* \* \* \*